United States Patent [19]

Ohnuma et al.

[11] Patent Number: 4,959,349

[45] Date of Patent: Sep. 25, 1990

[54] INDANE DERIVATIVE AND PERFUMERY COMPOSITION COMPRISING THE SAME

[75] Inventors: Hiroaki Ohnuma, Ichikai; Yoshiaki Fujikura, Utsunomiya; Manabu Fujita, Kashiwa; Nao Toi, Sakur, all of Japan

[73] Assignee: KAO Corporation, Tokyo, Japan

[21] Appl. No.: 483,881

[22] Filed: Feb. 23, 1990

[30] Foreign Application Priority Data

Mar. 3, 1989 [JP] Japan .................................... 1-51293
Mar. 3, 1989 [JP] Japan .................................... 1-51292
Mar. 6, 1989 [JP] Japan .................................... 1-53507

[51] Int. Cl.$^5$ .............................................. A61K 7/46
[52] U.S. Cl. ........................................ 512/14; 512/18; 560/255; 560/256; 568/819; 568/665; 568/659
[58] Field of Search .................... 512/14, 18; 560/255, 560/256; 568/819, 665, 659

[56] References Cited

U.S. PATENT DOCUMENTS

| | | | |
|---|---|---|---|
| 3,442,640 | 5/1969 | Wood et al. | 568/659 |
| 3,660,311 | 5/1972 | Wight | 512/14 |
| 3,681,464 | 8/1972 | Theimer | 568/665 |
| 3,927,083 | 12/1975 | Hall et al. | 512/14 |
| 4,250,200 | 2/1981 | Wiegers et al. | 568/659 |
| 4,535,192 | 8/1985 | Hall et al. | 568/819 |

*Primary Examiner*—James H. Reamer
*Attorney, Agent, or Firm*—Oblon, Spivak, McClelland, Maier & Neustadt

[57] ABSTRACT

Indane derivatives useful as fragrance-imparting components are disclosed. The represented indane derivatives by the formula (I),

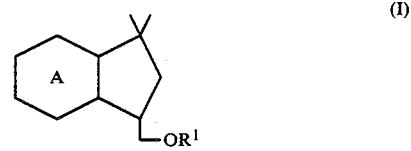

wherein ring A is a benzene or cyclohexane ring and $R^1$ is a hydrogen atom, an alkyl group having 1-4 carbon atoms, or an alkanoyl group having 1-6 carbon atoms, provided that when ring A is benzene, $R^1$ is a group other than hydrogen atom.

2 Claims, No Drawings

INDANE DERIVATIVE AND PERFUMERY COMPOSITION COMPRISING THE SAME

BACKGROUND OF THE INVENTION

1. Field of the Invention

The present invention relates to a novel indane derivative having an excellent odor and useful as a fragrance-imparting component of perfumes and to a perfumery composition comprising the same.

2. Description of the Background Art

A number of perfumery compounds have conventionally been known among compounds having the indane structure. Examples of such perfumery compounds have those having a musky odor, e.g. 1,1,2,3,3,8-hexamethyl-6-oxa-2,3,5,6,7,8-hexahydro-1H-benzo[f]indene (U.S. Pat. No. 4,162,256), 6-acetyl-1,1,2,3,3,5-hexamethylindane (FR Patent No. 1,392,804), 4-acethyl-1,1-dimethyl-6-tert-butylindane (U.S. Pat. No. 3,078,319); those having an indole-like odor, e.g. 4,4a,5,9b-tetrahydroindeno[1,2:d]-m-dioxine (DE Patent No. 714,645); those having a geranium- or magnolia-like odor, e.g. 2,4-dimethyl-4,4a,5,9b-tetrahydroindeno[1,2:d]-m-dioxine (FR Patent No. 1,577,817); and the like.

There are also many perfumery, compounds among reduced indanes having a bicyclo[4,3,0]nonane structure. They are, for example, 2-hydroxy-7,7,8,9,9-pentamethyl-bicyclo[4,3,0]nona-1(6)-ene having an earth-like woody odor (U.S. Pat. No. 3,636,165), 1-hydroxy-7,7,8,9,9-pentamethylbicyclo[4,3,0]nonane having a patchouli-like, camphoraceous odor, and 1-hydroxy-7,7,8,9,9-pentamethylbicyclo-[4,3,0]-nona-5-ene having a musky, patchouli-like, earth-like odor.

Since one odor of one compound is quite different from the odor of another compound having a very similar but slightly different chemical structure, it is very important to synthesize various compounds and examine their odors for producing new perfumeries.

In view of this, the present inventors have synthesized various compounds having the indane structure and the bicyclo[4,3,0]nonane structure and investigated their odors and their application as perfumes. As a result, the inventors have found that indane derivatives represented by the following formula (I) have excellent odors and are useful as a perfumery component of perfumes. This finding has led to the completion of this invention.

SUMMARY OF THE INVENTION

Accordingly, an object of the present invention is to provide an indane derivative represented by formula (I),

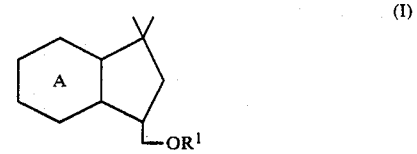

wherein ring A is a benzene or cyclohexane ring and $R^1$ is a hydrogen atom, an alkyl group having 1–4 carbon atoms, or an alkanoyl group having 1–6 carbon atoms, provided that when ring A is benzene, $R^1$ is a group other than hydrogen atom.

Another object of the present invention is to provide a perfumery composition comprising, as its perfume-imparting components, said indane derivative.

Other objects, features and advantages of the invention will hereinafter become more readily apparent from the following description.

DETAILED DESCRIPTION OF THE INVENTION AND PREFERRED EMBODIMENTS

In formula (I) which represents an indane derivative of the present invention, $R^1$ is a hydrogen atom, an alkyl group having 1–4 carbon atoms, or an alkanoyl group having 1–6 carbon atoms. Methyl, ethyl, propyl, iso-propyl, n-butyl, iso-butyl, and the like are given as examples of the alkyl group. The alkanoyl group includes formyl, acetyl, propionyl, butylyl, iso-butylyl, pentanoyl, iso-pentanoyl, and the like.

The following compounds are given as specific examples of indane derivatives of formula (I) 1,1-dimethyl-3-methoxymethylindane, 1,1-dimethyl-3-ethoxymethylindane, (1,1-dimethylindane-3-yl)methylfornate, (1,1-dimethylindane-3-yl)methylacetate, (1,1-dimethylindane-3-yl)methylpropiorate, 7,7-dimethyl-9-hydroxymethylbicyclo[4,3,0]nonane, and the like.

Compound (I) of this invention can be produced, for example, according to the following reaction scheme:

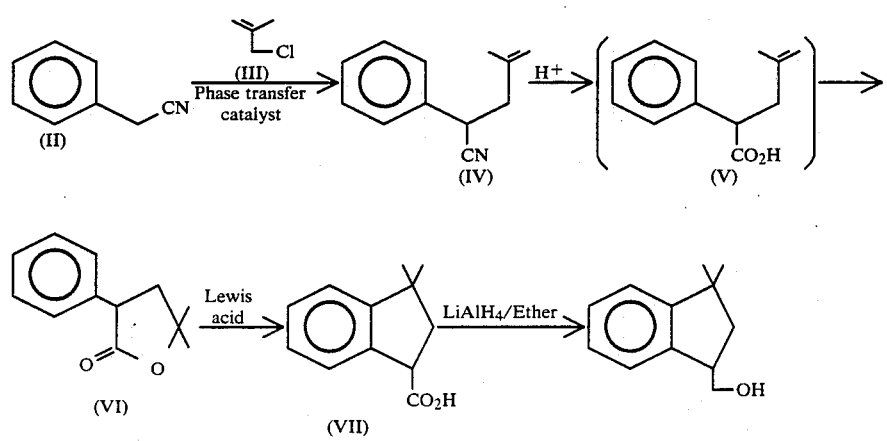

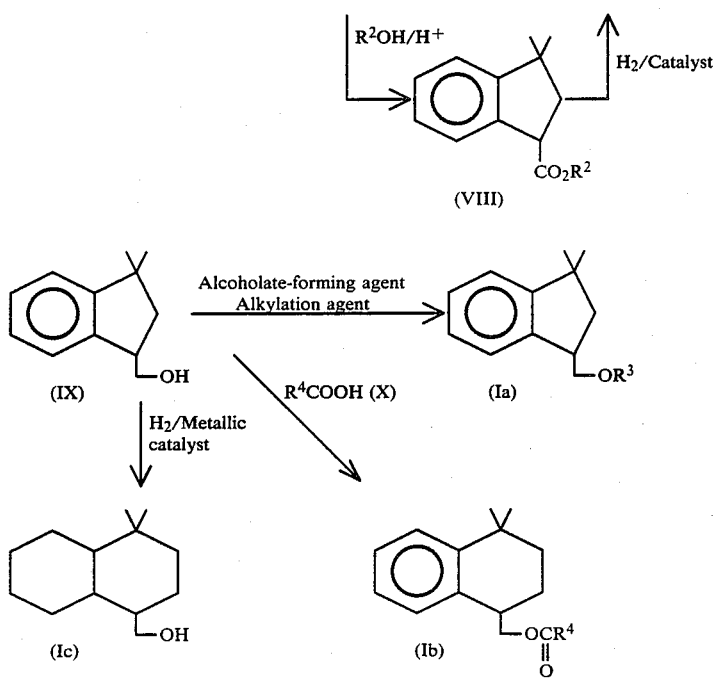

In the above formulae, $R^2$ is an alkyl group, $R^3$ is an alkyl group having 1–4 carbon atoms, and $R^4$ is a hydrogen atom or an alkyl group having 1–5 carbon atoms.

According to a known process [Makosza, *Org. Synth.*, 55, 91 (1976)], phenylacetonitrile (II) is reacted with methallyl chloride (III) in the presence of a phase transfer catalyst to produce 4-methyl-2-phenyl-4-pentenenitrile (IV). Triethylbenzylammonium chloride, tetra-n-butylammonium bromide, and the like are given as examples of a phase transfer catalyst. The amount of phenylacetonitrile (II) used in the above reaction is a 1–10 equivalent to methallyl chloride (III). The amount of a 2–10 equivalent is particularly preferable. A preferable amount of a phase transfer catalyst to be used is in the range of a 0.001–0.1 equivalent to methallyl chloride, with a 0.005–0.05 equivalent being particularly preferable. The reaction can be carried out at a temperature of 5°–50° C., preferably at 5°–30° C., in the presence of water and a caustic alkali.

The hydrolysis and cyclization reaction of 4-methyl-2-phenyl-4-pentenenitrile (IV) is then carried out by a single operation using an acid such as a dilute aqueous hydrochloric acid, a dilute aqueous sulfuric acid, or the like to produce 4,4-dimethyl-2-phenyl-4-butanolide (VI). The reaction can be carried out either with or without using a solvent such as an alcohol, e.g. methanol, ethanol; an organic acid, e.g. acetic acid, formic acid; and the like.

The lactone (VI) thus produced is reacted with a Lewis acid, e.g. aluminum chloride, aluminum bromide, to obtain 3-carboxy-1,1-dimethylindane (VII). A preferable amount of Lewis acid used is in the range of a 0.1–3.0 equivalent to the intermediate lactone (VI), with the range of a 1–3.0 equivalent being particularly preferable. Examples of preferable organic solvents used in the above reaction are dichloromethane, 1,2-dichloroethane, chloroform, and the like. The reaction is carried out at a temperature of 0°–50° C., preferably at 0°–40° C.

1,1-Dimethyl-3-hydroxymethylindane (IX) can be produced from carboxylic acid (VII), for example, by reducing the carboxylic acid using a reducing agent, e.g. lithium aluminum hydride, in an ether solution such as diethylether, tetrahydrofuran, or the like.

Another method of producing compound (IX) from carboxylic acid (VII) is refluxing the carboxylic acid and an alcohol, e.g. methanol, ethanol, under heating in the presence of an acid, e.g. sulfuric acid, p-toluene-sulfonic acid, to produce 3-alkoxycarbonyl-1,1-dimethylindane (VIII) and catalytically hydrogenating it in the presence of a catalyst, e.g. copper-chromium, copper-zinc The hydrogenation reaction can be performed without a solvent, or it can be carried out in the presence of a solvent such as a saturated hydrocarbon, e.g. n-hexane; an alcohol, e.g. methanol, ethanol; or the like. The amount of the catalyst used is 1–20% by weight of the ester (VIII) and the hydrogen pressure is 20–150 atom. The reaction can usually be performed at 80°–300° C. A temperature of 150°–250° C. is preferable in order to shorten the reaction time and to reduce production of by-products.

1,1-Dimethyl-3-hydroxymethylindane (IX) is the product described in U.S. patent application Ser. No. 07/421,129 and European Patent Application No. 89 119 438.3 filed by the present inventors.

An ether (Ia), which is one form of compound (I) of the present invention, can be prepared by reacting 1,1-dimethyl-3-hydroxymethylindane (IX) with an alcoholate forming agent in an organic solvent and then by reacting the product with an alkylation agent. Sodium hydride, sodium amide, sodium hydroxide, or the like is used as an alcoholate-forming agent in an amount of a 1.0–1.2 equivalent of compound (IX). Benzene, toluene, xylene, or the like can be used as a solvent. The alcholate-forming reaction can easily be carried out at a temperature of 30°–130° C. and completes in about 1–10 hours.

An alkyl halide such as methyl iocide, ethyl iodide, methyl bromide, ethyl bromide; an alkyl sulfate such as dimethyl sulfate, diethyl sulfate; and the like can be used as the alkylation agent in an amount of a 1.0–1.5 equivalent of compound (IX). The reaction is carried out at a temperature of 30°–130° C. and completes in about 1–10 hours.

After completion of the reaction, water is charged to the reaction mixture to separate the organic layer. The organic layer is washed with water and alkali and the solvent is evaporated. The residue is purified, for example, by distillation, HPLC, or the like to obtain 3-alkoxymethyl-1,1-dimethylindane (Ia).

An ester (Ib), which is another form of compound (I), can be prepared by reacting 1,1-dimethyline-3-hydroxymethylindane (IX) with a carboxylic acid (X) or its reactive derivative in the presence or absence of a solvent.

The carboxylic acids (IX) which can be used in the reaction include formic acid, acetic acid, propionic acid, n-butyric acid, iso-butyric acid, n-valeric acid, isovaleric acid, and the like. A reactive derivative of these carboxylic acids such as acid anhydrides or acid halides can also be used. An organic solvent which can be used is benzene, toluene, xylene, or the like. As a catalyst, an acid catalyst such as sulfuric acid, hydrochloric acid, p-toluenesulfonic acid, or boron fluoride etherate; a basic catalyst such as pyridine, dimethylaniline, triethylamine, sodium acetate; and the like can be used as required. The reaction is carried out at a temperature of 15°–150° C. and completes in about 1–20 hours.

After completion of the reaction, water is added to the reaction mixture to separate the organic layer. The organic layer is washed with water and the solvent is evaporated. The residue is purified, for example, by distillation, HPLC, or the like to obtain a 3-alkanoyloxy-1,1-dimethylindane (Ib).

A bicyclo[4,3,0]nonane (Ic), which is still another form of compound (I), can be prepared by catalytically hydrogenating 1,1-dimethyl-3-hydroxynethylindane (IX) using a metal catalyst in the presence or absence of a solvent.

A transition metal or its compound such as platinum oxide, Raney nickel, ruthenium carbon, or the like is preferably used in an amount of 1°–20% by weight based on the amount of compound (IX). A saturated hydrocarbon such as n-hexane, an alcohol such as methanol and ethanol is utilized when a solvent is to be used. The hydrogenation reaction may be carried out, for example, at a temperature of 80°–200° C. and under a hydrogen pressure of 20–150 atm.

Compound (Ic), 7,7-dimethyl-9-hydroxyethylbicyclo[4,3,0]nonane, can easily be obtained by the purification of the hydrogenated product by distillation, column chromatography, or the like.

Compound (Ic) thus prepared is usually a mixture of stereoisomers formed by hydrogenation reaction. Stereoisomers of a compound are commonly considered to have a somewhat different odor from each other. If necessary, the stereoisomers can be isolated by a conventional isolation method such as rectification, HPLC, and the like. Compound (Ic) of the present invention, however, usually does not require such an isolation procedure when it is used as a perfumery component.

When compound (Ic), 7,7-dimethyl-9-hydroxymethylbicyclo[4,3,0]nonane, is reacted with an alcoholate-forming agent and an alkylating agent according to the process described above, the corresponding ether compound can be obtained. Furthermore, the corresponding ester compound can be obtained, if Compound (Ic) is reacted with carboxylic acid (X) or its reactive derivative.

The indane derivatives of formula (I) of the present invention possess excellent floral, fruity, green, woody, or minty odor, and thus can be widely used as a fragrance imparting component for perfumes, soaps, shampoos, room air fresher, detergents, and the like either independently or in combination with other perfumery component.

Other features of the invention will become apparent in the course of the following description of the exemplary embodiments for preparing the intermediates and the compound of the present invention. It should be understood that these embodiments are given for illustration of the invention and are not intended to be limiting thereof.

EXAMPLES

Reference Example 1

Synthesis of 4-methyl-2-phenyl-4-pentenenitrile

[Compound (IV)]

To a mixed solution of 1,580 g (13.5 mol) of phenylacetonitrile, 11.3 g (5.0 mmol) of triethylbenzylammonium chloride and 1,200 ml of 50% aqueous sodium hydroxide wa dropwise added. 410 g (4.5 mol) of methallyl chloride over 2 hours while vigorously stirring and maintaining the temperature at 20°–30° C. After the addition, the mixture was stirred at the same temperature for one hour. 1,700 ml of water was added to the reaction mixture and the mixture was separated into an organic layer and a water layer. The organic layer was washed twice with 300 ml of saturated brine, once with 50 ml of 10% aqueous hydrochloric acid, and further twice with 100 ml of saturated brine, and dried over anhydrous sodium sulfate. The solvent was evaporated from the organic layer. The residue was distilled under reduced pressure to obtain 670 g (3.9 mol) of the title compound at a yield of 87% based on the fed methallyl chloride.

Boiling Point: 126°–130° C. 10 mmHg.

MS (Relative Intensity) 171 (M+, 24), 154 (6), 143 (26), 129 (13), 116 (58), 103 (11), 89 (12), 77 (11), 55 (100), 39 (29).

IR (neat, cm$^{-1}$) 3084, 2924, 2244, 1652, 1498, 1456, 902, 754, 700.

$^1$H-NMR (Solvent: CDCl$_3$, Internal standard method: TMS, δ) 7.32(5H, s), 5.0–4.7(2H, m), 3.92(1H, t, 8), 2.55(2H, d), 1.77(3H, s).

Reference Example 2

Synthesis of 4,4-dimethyl-2-phenyl-4-butanolide

[Compound (VI)]

385 g (2.2 mol) of 4-methyl-2-phenyl-4-pentenenitrile (IV) was refluxed under heating in 530 ml of water and 390 ml of concentrated sulfuric acid for 3 hours. The mixture was cooled to room temperature and 900 ml of water was added to it. The white crystals produced were separated by filtration under reduced pressure. The white crystals were washed twice with 500 ml of hexane and twice with 500 ml of warm water, followed by removal of the solvent to obtain 300 g (1.6 mol) of the title compound at a yield of 70%.

Melting Point: 66.0°–66.8° C.

MS (Relative Intensity) 190 (M+, 2), 175 (6), 146 (M+—CO2, 54), 131 (100), 116 (6), 104 (16), 91 (34), 77 (12), 51 (12), 43 (83).

IR (KBr tablet, cm$^{-1}$). 2984, 1776, 1378, 1264, 1142, 958, 706, 692.

$^1$H-NMR (Solvent: CDCl$_3$, Internal standard method: TMS, δ) 7.35–7.20(5H, m), 4.00(1H, dd, 9, 12), 2.53(1H, dd, 9, 13), 2.18(1H, dd, 12, 13), 1.49(3H, s), 1.44(3H, s).

$^{13}$C-NMR (CDCl$_3$, TMS, δ) 176.2(s), 137.3(s), 128.6(d), 128.0(d), 127.2(d), 81.8(s), 46.7(d), 43.7(t), 28.7(q), 26.7(q).

Reference Example 3

Synthesis of 3-carboxy-1,1-dimethylindane

Compound (VII)]

117 g (0.615 mol) of 4,4-dimethyl-2-phenyl-4-butanolide (VI) dissolved in 200 ml of 1,2-dichloroethane was added under ice-cooling over one hour to 164 g (1.23 mol) of anhydrous aluminum chloride dissolved in 200 ml of 1,2-dichloroethane. The mixture was stirred for 2 hours, charged into 1,000 ml of ice water, and extracted with 500 ml of chloroform. The organic layer was washed twice with 500 ml of water and dried over anhydrous sodium sulfate. The solvent was removed from the organic layer and the residue was distilled under reduced pressure to produce 96 g of the title compound (VII) at a yield of 82% for the fed lactone.

Boiling Point: 152°–153° C./3 mmHg.

MS (Relative Intensity) 190 (M+, 44), 175 (100), 145 (26), 129 (70), 115 (15), 91 (11), 77 (7), 63 (5), 51 (7), 39(6).

IR (Liquid film, cm$^{-1}$) 3028, 2960, 1710, 1482, 1418, 1306, 1228, 928, 762.

$^1$H-NMR (Solvent: CDCl$_3$, Internal standard method: TMS, δ) 12.07(1H, brs), 7.40(1H, d, 7), 7.3–7.1(3H, m), 4.13(1H, t, 8), 2.32(1H, dd, 8, 13), 2.23(1H, dd, 8, 13), 1.38(3H, s), 1.23(3H, s).

$^{13}$C-NMR (CDCl$_3$, TMS, δ) 180.9(s), 152.4(s), 138.4(s), 128.0(d), 126.8(d), 125.0(d), 122.3(d), 47.8(d), 44.1(t), 43.5(s), 29.5(q), 29.0(q).

Reference Example 4

Synthesis of 1,1-dimethyl-3-hyproxymethylindane

[Compound (IX)]

[A] A mixed solution of 100 g (0.53 mol) of 3-carboxy-1,1-dimethylindane (VII) and 300 ml of ether was added dropwise to a solution of 25 g (0.66 mol) of lithium aluminum hydride in 300 ml of ether under ice-cooling over one hour. After the addition, the mixture was mildly refluxed under heating for one hour. To the reaction mixture was added 25 ml of water, 25 ml of 15% aqueous sodium hydroxide, and 75 ml of water in that order to hydrolyze the excess lithium aluminum hydride. The white precipitate produced was eliminated by filtration under reduced pressure. The filtrate was distilled under reduced pressure to obtain 89 g (0.51 mol) of the title compound at a yield of 96%.

Boiling Point: 108° C./2.5 mmHg.

MS (Relative Intensity) 176 (M+, 28), 161 (12), 145 (100}, 143 (29), 128 (23), 117 (13), 105 (6), 91 (11), 77 (5).

IR (Liquid film, cm$^{-1}$) 3370, 2956, 2866, 1482, 1026, 759, 744.

$^1$H-NMR (CDCl$_3$, TMS, δ) 7.3–7.1(4H, m), 4.0–3.8(2H, m), 3.41(1H, m), 2.13(1H, dd, 7, 12), 1.78(1H, dd, 7, 12), 1.54(1H, brs), 1.36(3H, s), 1.21(3H, s).

$^{13}$C-NMR (CDCl$_3$, TMS, δ) 153.2(s), 142.4(s), 127.2(d), 126.4(d), 123.8(d), 122.3(d), 66.1(t}, 44.9(d), 44.9(t), 43.0(s), 29.9(q), 29.3(q).

[B] (1) 100 g (0.53 mol) of 3-cartoxy-1,1-dimethylindane (VII) was added to a mixture of 60 ml of methanol and 500 ml of dichloroethane. The mixture was refluxed under heating for hours in the presence of 1.5 ml of sulfuric acid as a catalyst. The reaction mixture was allowed to cool and diluted with water to separate an organic layer and a water layer. The organic layer was washed with aqueous sodium bicarbonate and dried. The solvent was evaporated and the residue was distilled under reduced pressure to obtain 103 g (0.50 mol) of 1,1-dimethyl-3-methoxycarbonylindane [the compound having CH$_3$ for R$^2$ in formula (VIII)] at a yield of 95%.

Boiling Point: 118° C./5 mmHg.

MS (Relative Intensity) 204 (M+, 40), 189 (71), 157 (12), 145 (76), 130 (21), 129 (100), 128 (17), 115 (12), 91 (8).

$^1$R (Liquid film, cm$^{-1}$) 2956, 1743, 1482, 1167, 762.

$^1$H-NMR (CDCl$_3$, TMS, δ) 7.4–7.1(4H, m), 4.10(1H, t, 8), 3.75(3H, s), 2.31(1H, dd, 8, 13), 2.19(1H, dd, 8, 13), 1.37(3H, s), 1.21(3H, s).

$^{13}$C-NMR (CDCl$_{13}$, TMS, δ) 174(s), 152(s), 139(s), 128(d), 127(d), 125(d), 122(d), 52(q), 48(d), 44(t), 43(s), 29.5(q), 29(q).

(2) A mixture of 50 g (0.24 mol) of 1,1-dimethyl-3-methoxycarbonylindane (VIII) obtained in (1) above and 5 g of a copper-chromium catalyst was placed in a 100 ml autoclave. After internal air was displaced by hydrogen the mixture was heated at an initial hydrogen pressure of 100 kg/cm$^2$. The reaction temperature reached 230° C. 30 minutes after the heating was started. The absorption of hydrogen terminated when the reaction was continued at this temperature for 8 hours. After the reaction, the mixture was cooled, the pressure was released, and the catalyst was separated by filtration. The filtrate was distilled under reduced pressure to produce 35 g (0.20 mol) of the title compound at a yield of 82%.

EXAMPLE 1

Synthesis of 1,1-dimethyl-3-methoxymethylindane [Compound having CH$_3$ for R$^1$ of formula (I)]

A solution of 17.25 g (0.43 mol) of 60% sodium hydride in 500 ml of xylene was heated to 100° C. To this was dropwise added over 2 hours a mixture of 69 g (0.39 mol) of 1,1-dimethyl-3-hydroxymethylindane (IX) and 250 ml of toluene. After stirring for 5 hours, 27.1 g (0.215 mol) of dimethyl sulfate was added dropwise to the reaction mixture over 2 hours. After the addition, the mixture was stirred for 3 hours to complete the reaction. 250 ml of water was added to the resulting reaction mixture to separate the water and organic layers. The organic layer was washed with water, an aqueous solution of sodium sulfate, and saturated brine, and dried over anhydrous magnesium sulfate. After removing the solvent, the residue was distilled under reduced pressure to produce 68.3 g (0.36 mol) of 1,1-dimethyl-3-methoxymethylindane at a yield of 92%. The product was a colorless, transparent liquid having a green, herbal, woody odor.

Boiling Point: 81.0°–81.5° C./2 mmHg.

MS (Relative Intensity) 190 (M+, 18), 175 (5), 145 (100), 143 (15), 128 (13), 117 (11), 115 (7), 105 (4), 91 (7), 45 (6).

IR (Liquid film, cm$^{-1}$) 2960, 2928, 1482, 1456, 1106, 762, 748.

$^1$H-NMR (CDCl$_{13}$, TMS, δ) 7.3–7.1(4H, m), 3.69(4H, m), 3.47(2H, m), 3.40(3H, s), 2.13(1H, dd, 12, 7), 1.67(1H, dd, 12, 8), 1.35(3H, s), 1.19(3H, s).

EXAMPLE 2

Synthesis of 1,1-dimethyl-3-ethoxymethylindane

[Compound having C$_2$H$_5$ for R$^1$ of formula (I)]

The reaction was carried out in the same manner as in Example 1, except that 33.2 g (0.215 mol) of diethyl sulfate was used instead of dimethyl sulfate. The resulting reaction mixture was processed in the same manner as in Example 1 and distilled under reduced pressure to produce 69.3 g (0.34 mol) of 1,1-dimethyl-3-ethoxymethylindane at a yield of 87%. The product was a colorless, transparent liquid having fruity, woody, and spicy odor with a slightly green tint.

Boiling Point: 89.0°–89.5° C./2 mmHg.

MS (Relative Intensity) 204 (M+, 15), 189 (3), 145 (100), 128 (10), 117 (9), 105 (3), 91 (7), 59 (4).

$^1$R (Liquid film, cm$^{-1}$) 2960, 2864, 1482, 1480, 1456, 1112, 762, 748.

1H-NMR (CDCl$_3$, TMS, δ) 7.3–7.1(4H, m), 3.73(1H, m), 3.54(2H, q, 7), 3.48(2H, m), 2.15(1H, dd, 13, 7), 1.67(1H, dd, 13, 7), 1.34(3H, s), 1.24(3H, t, 7), 1.19(3H, s).

EXAMPLE 3

Synthesis of (1,1-dimethylindane-3-yl)methylformate

[Compound having CHO for R$^1$ of formula (I)]

17.6 g (0.1 mol) of 1,1-dimethyl-3-hydroxymethylindane (IX) and 46.0 g (1.0 mol) of formic acid were reacted at room temperature for 16 hours while stirring. After the reaction, surplus formic acid was removed under reduced pressure. The residue was extracted with ether, washed with aqueous sodium bicarbonate, and dried over anhydrous magnesium sulfate. The solvent was removed from the organic layer and the residue was distilled under reduced pressure to produce 16.8 g (0.82 mol) of (1,1-dimethylindane-3-yl)methylformate at a yield of 82%. The product was a colorless, transparent liquid having a woody, green odor similar to green tea with a scent of rush.

Boiling Point: 114°–116° C./4 mmHg.

MS (Relative Intensity) 204 (M+, 1), 189 (1), 158 (46), 145 (30), 143 (100), 128 (32), 117 (8), 115 (11), 91 (9), 77 (4).

IR (Liquid film, cm$^{-1}$) 2960, 2868, 1730, 1482, 1456, 1176, 762.

$^1$H-NMR (CDCl$_3$, TMS, δ)

8.09(1H, s), 7.25–7.15(4H, m), 4.45(1H, dd, 11, 6), 4.34(1H, dd, 11, 6), 3.56(1H, m), 2.15(1H, dd, 13, 8), 1.72(1H, dd, 13, 8), 1.36(3H, s), 1.20(3H, s).

EXAMPLE 4

Synthesis of (1,1-dimethylindane-3-yl)methylacetate
[Compound having CH$_3$CO for R$^1$ of formula (I)]

To a mixture of 12.3 g (70 mmol) of 1,1-dimethyl-3-hydroxymethylindane (IX), 12.8 g of dimethylpyridine, and 20 ml of toluene, 8.6 g (84 mmol) of acetic acid was added dropwise over 10 minutes at room temperature. After the addition, the mixture was stirred for 5 hours at 30° C. to complete the reaction. After extraction with ether and removal of dimethylpyridine with 10% sulfuric acid, the residue was dried over anhydrous magnesium sulfate. The solvent was removed from the organic layer and the residue was distilled under reduced pressure to produce 11.6 g (53 mmol) of (1,1-dimethylindane-3-yl)methylacetate at a yield of 76%. The product was a colorless, transparent liquid having a woody, floral odor with a weak fruity sensation.

Boiling Point: 107° C./1 mmHg.

MS (Relative Intensity) 158 (51), 143 (100), 128 (22), 117 (7), 115 (9), 91 (7), 115 (9), 91 (7), 43 (22).

IR (Liquid film, cm$^{-1}$) 2960, 1747, 1245, 1232, 1039, 768, 752.

$^1$H-NMR (CDCl$_3$, TMS, δ) 7.25–7.10(4H, m), 4.35(1H, dd, 11, 7), 4.22(1H, dd, 11, 7), 3.52(3H, s), 2.14(1H, dd, 13, 8), 2.06(3H, s), 1.68(1H, dd, 13, 8), 1.35(3H, s), 1.20(3H, s).

EXAMPLE 5

Synthesis of (1,1-dimethylindane-3-yl)methylpropionate

Compound having C$_2$H$_5$CO for R$^1$ of formula (I)]14.1 g (61 mmol) of (1,1-dimethylindane-3-yl)methylpropionate was prepared at a yield of 87% in the same manner as in Example 4, except that propionic anhydride was used instead of acetic anhydride. The product was a colorless, transparent liquid having a weak fruity, woody Boiling Point: 116° C./1 mmHg.

MS (Relative Intensity) 158 (53), 145 (22), 143 (100), 128 (16), 117 (7), 115 (6), 91 (5), 57 (14).

IR (Liquid film, cm$^{-1}$) 2960, 1740, 1184, 1084, 1022, 762, 748.

$^1$H-NMR (CDCl$_3$, TMS, δ)
7.25–7.10(4H, m), 4.35(1H, dd, 11, 7), 4 24(1H, dd, 11, 7), 3.53(3H, m), 2.36(2H, q, n), 2.14(1H, dd, 13, 8), 1.69(1H, dd, 13, 8), 1.35(3H, s), 1.20(3H, s), 1.15(3H, t, 7).

EXAMPLE 6

Synthesis of 7,7-dimethyl-9-hydroxymethylbicyclo[4,3,0]nonane [Compound (Ic)]

11.3 g (64 mmol) of 1,1-dimethyl-3-hydroxymethylindane (IX), 3 g of 5% luthenium-carbon (manufactured by Engerhard Industries Corp.), and 300 ml of ethanol was placed in a 100 ml autoclave. After internal air was displaced by hydrogen, the mixture was heated at an initial hydrogen pressure of 100 kg/cm$^2$. The reaction temperature reached 140° C. 1 hour after the heating was started. The absorption of hydrogen terminated when the reaction was continued at this temperature for 7 hours. After cooling, the pressure was released and the catalyst was separated out by filtration. The filtrate was distilled under reduced pressure to produce 9.7 g (53 mmol) of the title compound (Ic) at a yield of 83%. Capillary gas chromatography analysis revealed that the compound is comprised of two major components each having a peak of which the area ratio was 59:41.

Boiling Point: 97° C./0.9 mmHg.

Elemental Analysis: for C$_{12}$H$_{22}$O Found: C 79.10, H 12.18, Calculated: C 79.06, H 12.16.

MS (Relative Intensity).

[A major component having a 55% peak]167 (2), 164 (3), 149 (100), 123 (41), 108 (92), 95 (55) 81 (50), 69 (56), 55 (37), 41 (51).

]A major component a 41% peak]167 (10), 164 (3), 151 (37), 126 (35), 108 (190) 95 (57), 82 (69), 67 (60), 55 (39), 41 (54).

IR (Liquid film, cm$^{-1}$) 3340, 2940, 2873, 1460 1369, 1021.

$^1$H-NMR (CDCl$_3$, TMS δ): for the isomer mixture 3.714 3.4(2H, m), 2.35–2.0)3H, m), 1.85–1.15(11H, m), 0.98(3H, s), 0.92(3H, s).

EXAMPLE 7

| Bouquet-type perfumery composition | |
|---|---|
| | Parts by weight |
| Orange oil Perra | 50 |
| Linalool | 100 |
| Petitgrain oil Paraguay | 20 |
| Aldehyde C-10 | 10 |
| Aldehyde C-11 Undecylenic | 10 |
| Aldehyde C-12 | 10 |
| Citronellol | 100 |
| Phenylethyl alcohol | 100 |
| Lirhal *1 | 50 |
| Benzyl acetate | 50 |
| Hexylcinnamic aldehide | 100 |
| Eugenol | 20 |
| γ-Methylionone | 100 |
| Coumarin | 100 |
| Vanillin | 10 |
| Musk ketone | 70 |
| Total | 900 |

*1 Lirhal: Trademark, manufactured by IFF Co.; 4-(4-hydroxy-4-methylpentyl)-3-cyclohexene-1-carboaldehyde To 900 parts by weight of the above perfumery composition 100 parts by weight of 1,1-dimethyl-3-methoxymethylindane was added to prepare a bouquet-type perfumery composition which gave a fresh order with a greenish mild sweetness.

EXAMPLE 8

| Hay-type perfumery composition | |
|---|---|
| | Parts by weight |
| Acetophenone | 30 |
| Linalool | 100 |
| Lavender oil Montblank 40/42 | 70 |
| Benzyl acetate | 100 |
| α-Ionone | 100 |
| γ-Methylionone | 100 |
| Cedar wood oil Virginia | 100 |
| Methyleugenol | 50 |
| Coumarin | 100 |
| Benzophenone | 50 |
| Total | 800 |

To the above perfumery composition 200 parts by weight of (1,1-dimethylindane-3-yl)methylformate was added to prepare a hay-type perfumery composition having a warm, green, and rich odor.

EXAMPLE 9

| Rose-type perfumery composition | |
|---|---|
| | Parts by weight |
| Hexanol | 40 |
| Rose oxide | 5 |
| Citral | 5 |
| l-Menthol | 10 |
| Styrally acetate | 30 |
| Geraniol | 100 |
| Citronellol | 200 |
| Phenylethyl alcohol | 390 |
| Eugenol | 20 |
| γ-Methylionone | 50 |
| Guaiac wood oil | 50 |
| Total | 900 |

To 900 parts by weight of the above perfumery composition 100 parts by weight of 7,7-dimethyl-9-hydroxymethylbicyclo[4,4,0]nonane was added to prepare a rose-type perfumery composition having a fresh floral odor with a natural sweetness.

Obviously, numerous modifications and variations of the present invention are possible in light of the above teachings. It is therefore to be understood that within the scope of the appended claims, the invention may be practiced otherwise than as specifically described herein.

What is claimed is:

1. An indane derivative represented by formula (I),

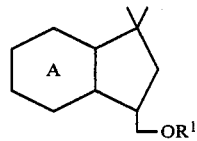

(I)

wherein ring A is a benzene or cyclohexane ring and R$^1$ is a hydrogen atom, an alkyl group having 1–4 carbon atoms, or an alkanoyl group having 1–6 carbon atoms, provided that when ring A is benzene R$^1$ is a group other than hydrogen atom.

2. A perfumery composition comprising as its fragrance imparting component an indane derivative represented by formula (I),

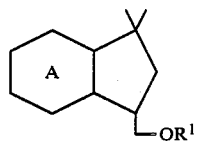

(I)

wherein ring A is a benzene or cyclohexane ring and R$^1$ is a hydrogen atom, an alkyl group having 1–4 carbon atoms, or an alkanoyl group having 1–6 carbon atoms, provided that when ring A is benzene, R$^1$ is a group other than hydrogen atom.

* * * * *